United States Patent [19]

Tsukamoto

[11] Patent Number: 4,856,326
[45] Date of Patent: Aug. 15, 1989

[54] APPARATUS FOR MEASURING AN ADHESION FORCE OF A THIN FILM

[75] Inventor: Yuji Tsukamoto, Tokyo, Japan

[73] Assignee: NEC Corporation, Japan

[21] Appl. No.: 224,306

[22] Filed: Jul. 26, 1988

[30] Foreign Application Priority Data

Jul. 27, 1987 [JP] Japan ................................. 62-188193

[51] Int. Cl.$^4$ .............................................. G01N 3/34
[52] U.S. Cl. ...................................... 73/150 A; 73/12; 73/799; 73/801
[58] Field of Search ............... 73/799, 801, 82, 150 A, 73/12

[56] References Cited

U.S. PATENT DOCUMENTS 4,606,225  8/1986  Thomason et al. ............... 73/150 A

OTHER PUBLICATIONS

"Adhesion of TiC and Ti(C,N) Coatings on Steel", Steinmann, P. A., Hintermann, H. E., J. Vac. Sci. Technol. A 3(6), Nov./Dec. 1985.

Primary Examiner—Jerry W. Myracle
Attorney, Agent, or Firm—Leydig, Voit & Mayer

[57] ABSTRACT

An apparatus for measuring the adhesion force of a thin film deposited on a substrate of a specimen. The apparatus comprises an inclining mechanism for mounting a sample dish with a specimen inclined by a predetermined angle with respect to the sample dish, an indentor disposed above the specimen for deforming the specimen by indentation, a driver for driving the indentor perpendicular to the sample dish, a load transducer for measuring a load applied to the specimen by the indentor, a sensor for sensing propagation of a crack produced in the specimen by the load, a displacement gage interlocked with the driver for measuring a penetration depth of the indentor, and a measuring mechanism for measuring the adhesion force of the thin film to the substrate.

12 Claims, 4 Drawing Sheets

APPARATUS FOR MEASURING AN ADHESION FORCE OF A THIN FILM

BACKGROUND OF THE INVENTION

The present invention relates to an apparatus for measuring an adhesion force of a thin film to a substrate.

Thanks to the progress of film forming technology, many kinds of thin films are extensively used in a variety of fields as magnetic materials, electronic materials and corrosion-resistant materials. A problem with such a thin film device is that the thin film is apt to come off its associated substrate or another thin film in various situations, e.g., when the film is relatively thick, when the film is constituted multiple layers each being made of a different material, when the surface of the film suffers from some contamination during the course of production, and when the use of materials which do not match each other is unavoidable for the substrate and thin film. The separation of the substrate and the thin film during the course of manufacturing immediately leads to a decrease in yield and an increase in cost. Another problem with the thin film device is the separation of the thin film due to heat and corrosion which depend upon the ambient conditions. Separation ascribable to temperature variation and the corrosion often effect the resistivity to environment and long-term reliability of the thin film.

For the improvement in quality control and reliability, therefore, there is a keen demand for a method capable of measuring an adhesion force of the thin film with high accuracy and thereby promoting quantitative analysis of separation tendency of the thin film.

Some elaborated methods have heretofore been proposed for the measurement of the adhesion forces of thin film to the substrate. All the conventional methods are of the sort measuring a force or energy needed to remove a thin film from the substrate and may generally be classified into five types, i.e., (1) an adhesion type method, (2) a scratch type method, (3) a centrifugal force type method, (4) a ultrasonic wave type method, and (5) an electromagnetic tension type method. Of these five different methods, the scratch type method is predominant presently because it is superior in the quantitative nature and reproducibility of data.

The scratch type method is such that a hard stylus is pressed against a thin film under a certain load and then moved to scratch the thin film from a substrate, as described in the article "Adhesion of TiC and Ti(C,N) coatings on steel" by P. A. Steinmann et al. (J. Vacuum Science Technology, A3 (6), pages 2394–2400, issued 1985). In this method, the greatest shearing force acts in edge portions of an indent which is formed by the stylus and the separation proceeds at the edge portion. The stylus has a tip made by diamond, sapphire or similar hard material and provided with an appropriate radius of curvature. The adhesion force acting between the thin film and the substrate is defined as a load which forms the scratch on the surface of the thin film or a load which sharply increases the coefficient of friction.

The scratch type measuring apparatus further includes an acoustic emission (AE) sensor for measuring the adhesion force. The AE sensor measures the adhesion force by causing the diamond stylus to scratch the surface of the thin film at a constant speed. The load acting on the thin film is sequentially increased from 1 to 200N at a predetermined rate (usually 100N/min) during one scratching operation. As the scratching operation proceeds under the increasing load, the AE sensor mounted on an indenter holder produces an AE signal which is associated with destruction in the thin film or at the boundary between the thin film and the substrate. A particular load which causes the AE signal to sharply increase (hereinafter referred to as a critical load) is defined as the adhesion force of the thin film.

The conventional apparatus for the measurement of the adhesion force have various problems left unsolved. Since the critical load measured by the scratch type method is complicatedly dependent upon the hardness of the substrate and the thickness of the thin film, maintaining consistent substrate hardness and film thickness is required to measure the critical loads. Another requirement for the measurement of the critical loads is that the surfaces of the substrates and the thin films be individually finished in the same condition because the surface roughness of the substrates and the thin films also has influence on the critical load.

Further, the conventional apparatus can measure the thin film thickness up to micron range. However, the measurement in the micron thickness range is unsatisfactory for the current thin film forming technology which has reached a submicron thickness range. In the scratch type measurement to a ductile material, a swell is formed by the stylus so as to increase the coefficient of friction and cause the acoustic emissions and, therefore, it is difficult to evaluate the adhesion forces of highly ductile thin films by the scratch type measurement. For the reasons described above, the applicable range of the scratch type measurement is limited to oxide films, nitride films and carbide films which are relatively hard and lie in the micron thickness range.

SUMMARY OF THE INVENTION

It is, therefore, an object of the present invention to provide an apparatus capable of measuring adhesion forces of thin films whose thickness lie in the submicron range. Accordingly, the present invention provides an apparatus for measuring an adhesion force of a thin film, the apparatus comprising an inclining mechanism, an indentor, a driver, a load transducer, a sensor, and a displacement gage. The inclining mechanism is used for mounting a sample dish with a specimen that includes a substrate and a thin film deposited on the substrate. The specimen is inclined at a predetermined angle with respect to the sample dish. The indentor is disposed above the specimen and serves to deform the specimen by indentation. The driver drives the indentor perpendicularly to the sample dish and the load transducer measures the load applied to the specimen by the indentor. The sensor senses propagation of a crack produced in the specimen by the load and the displacement gage is interlocked with the driver for measuring a penetration depth of the indentor. The apparatus further comprises a measuring mechanism for measuring the adhesion force of the thin film to the substrate on the basis of the load, the predetermined angle, and the penetration depth at the time when the sensor produces a sense signal.

The present invention further provides an apparatus for determining an adhesion force of a thin film of a substrate, the apparatus comprising a sample dish, an inclining mechanism, an indentor, a driver, a load transducer, an acoustic emission transducer, and a displacement gage. The inclining mechanism is mounted on the sample dish and inclines the specimen by a predetermined angle with respect to the sample dish. The indentor is disposed above the specimen and serves to deform the specimen by indentation. The driver is connected to the indentor and drives the indentor against the specimen, thereby applying a load to the specimen. The load transducer measures the load applied to the specimen by the indentor, and the sample dish is mounted on the load transducer. The acoustic emission transducer senses propagation of a crack produced in the specimen by the load. The displacement gage is cooperatively arranged with the driver for measuring the penetration depth of the indentor. The apparatus further comprises a measuring mechanism coupled to the load transducer and the acoustic emission transducer for measuring the adhesion force of the thin film.

With any of the constructions described above, the present invention is capable of measuring an adhesion force of the thin film having a thickness of even less than 1 micron and made of various materials.

The principle of measurement in accordance with the present invention is based on the fact that the number, amplitude and frequency of an AE signal associated with destruction or separation depends upon the location where the destruction or the separation occurs, i.e. within the substrate, within the thin film or at the boundary between the substrate and the thin film.

In the indentation type apparatus described above, the indenter is implemented by an AE transducer with a sharp spherical tip so as to increase the measurement sensitivity to the acoustic emissions. The load acting on the specimen through the indenter and the penetration depth of the indenter are controlled and measured with considerable accuracy to sense the AE signal which is ascribable to the separation of the thin film from the substrate. The inclining mechanism is adapted to apply shearing stress to the boundary between the thin film and the substrate. The shearing stress $\tau$ acting on the boundary in the event of the separation is expressed as:

$$\tau = (W/\delta^2) \cdot \cos \alpha \tag{1}$$

where W denotes an instantaneous load applied at the time when the AE signal indicates the separation of the thin film from the substrate, $\delta$ denotes a penetration depth of the indenter of the same instant, and $\alpha$ denotes an angle of a specimen with respect to the horizontal. The adhesion force is determined in terms of the value of $\tau$.

BRIEF DESCRIPTION OF THE DRAWINGS

In the drawings, the same or similar structural elements denote the same or similar reference numerals.

DESCRIPTION OF THE PREFERRED EMBODIMENTS

Figure 1:
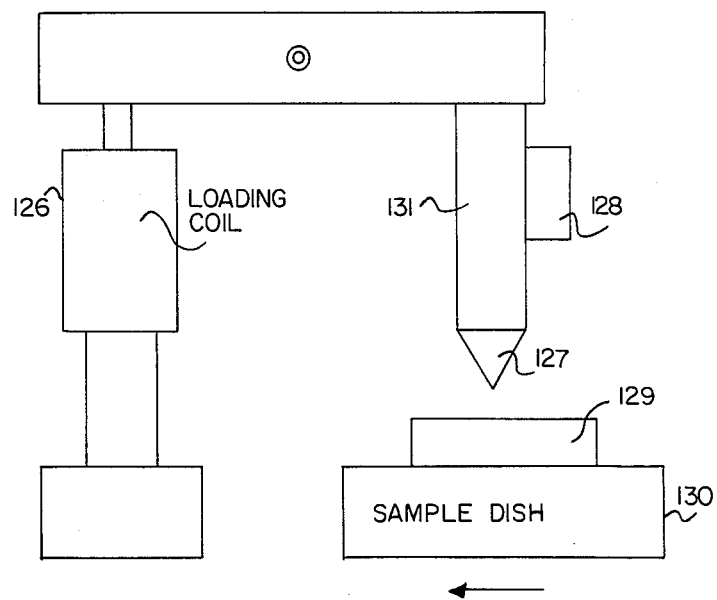
FIG. 1 is a side view showing a conventional apparatus for measuring an adhesion force of a thin film.

In order to facilitate the understanding of the present invention, a brief reference will be made to the conventional apparatus for measuring an adhesion force of a thin film with reference to FIG. 1. The apparatus includes a sample dish 130 on which a specimen 129 is securely mounted and a diamond stylus 127 for scratching the surface of the specimen 129 at a constant speed, the specimen 129 being coated with a thin film.

A loading coil 126 is provided for increasing the load from 1N to 200N at a predetermined rate (usually 100N/min) during the course of approximately one scratching. An acoustic emission (AE) sensor 128 is mounted on a stylus holder 131 to sense an AE signal representative of destruction which occurs within the thin film or at the boundary between the thin film and the substrate of the specimen 129 as the scratching proceeds with the load being increased. A particular degree of load which causes the AE signal to sharply rise (hereinafter referred to as critical load) is regarded as being representative of an adhesion force of the thin film.

The prior art measuring apparatus described above suffers from various drawbacks as discussed earlier.

Figure 2:
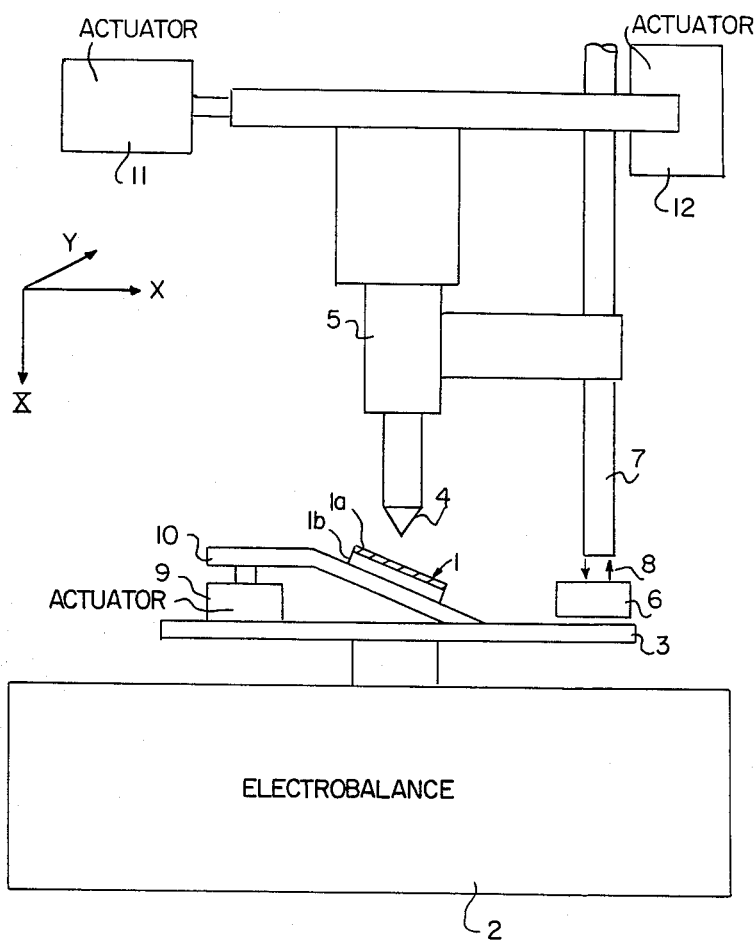
FIG. 2 is a side view showing a first embodiment of the present invention.

Referring to FIG. 2, an embodiment of the present invention includes an electrobalance or load transducer 2 atop of which a sample dish 3 is provided. The sample dish 3 is loaded with a specimen 1 which is coated with a thin film 1a. An indenter 4 is implemented by a PZT (plumbum-zironic acid-titanic acid piezoelectric ceramic) AE transducer which is sharpened to form a spherical tip with a tip radius of 10 microns by machining and ion milling which follows the machining. The indenter 4 is fitted to the tip of a piezoelectric actuator 5 to deform the specimen 1 by indentation and to sense an AE signal representative of destruction which occurs in the thin film or at the boundary between the thin film 1a and the substrate 1b of the specimen 1. A Photonic Probe (tradename and available from Photonics, U.S.A.) 7 is provided integrally with the indenter 4. Light issuing from the Probe 7 is reflected by a mirror 6 which is mounted on the sample dish 3 to return to the Probe 7. The distance between the probe 7 and the mirror 6, i.e., the amount $\delta$ of penetration of the indenter 4 into the specimen 1 is measured in terms of the intensity of reflection from the mirror 6. The load W acting on the specimen 1 is measured by the electrobalance 2. A piezoelectric actuator 9 serves as a driver for driving an inclining mechanism 10 which is adapted to incline the specimen 1 so as to determine an angle $\alpha$ of the specimen 1. Piezoelectric actuators 11 and 12 are provided for moving the piezoelectric actuator 5 in X and Y directions in a horizontal plane. Specifically, the actuators 11 and 12 are capable of moving the indenter 4 to any desired position on the specimen 1 to measure an adhesion force thereof. This allows the indenter 4 to be accurately positioned at desired portion of the surface of the specimen 1. The adhesion force can be measured by the aforementioned formula (1).

Figure 3:
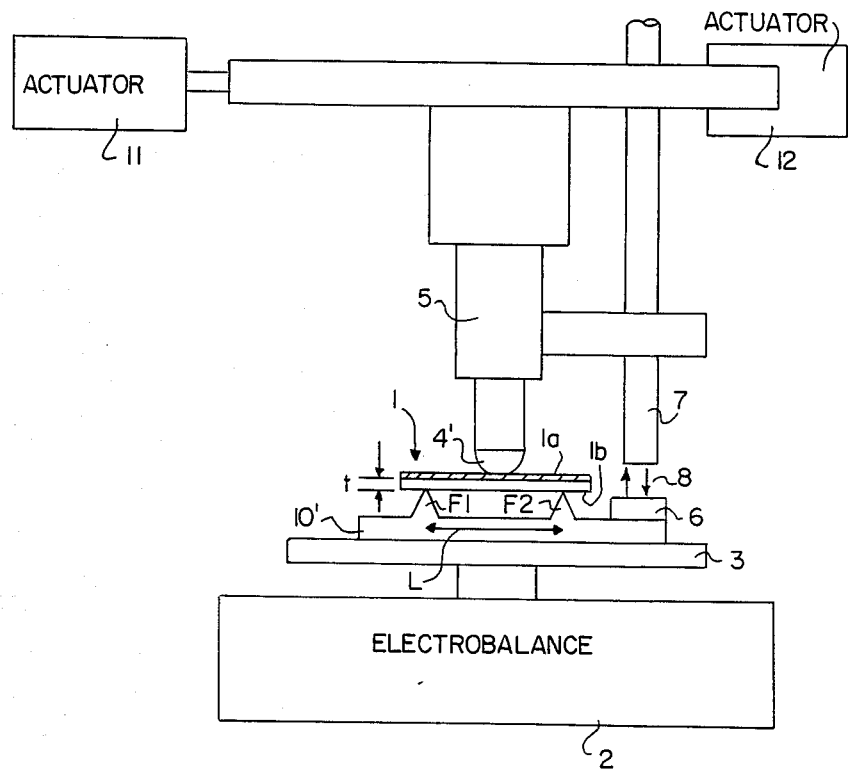
FIG. 3 is a side view showing a second embodiment of the present invention.

Referring to FIG. 3, a second embodiment of the invention is shown which is of a bending test type.

In the bending test type apparatus, the indentor is also implemented by an AE transducer and the adhesion force of a thinned film is measured by bending a specimen which is supported by a fulcrum mechanism. The maximum bending stress sigma acting on the boundary between a thin film and a substrate due to the bending moment is represented by:

$$\sigma = 3WL/2bt^2 \tag{2}$$

where W denotes an instantaneous load at the time when the AE signal indicates the separation of the thin film from the substrate, L denotes a distance between fulcrums of the flucrum mechanism, b denotes a width of the substrate, and t denotes a thickness of the substrate. The adhesive force is measured in terms of the bending stress $\sigma$.

In FIG. 3, the same or similar structural elements as those of the first embodiment will not be described to avoid redundancy. In this embodiment, a fulcrum mechanism 10′ is provided in place of the inclining mechanism 10 of the first embodiment. The fulcrum mechanism 10′ has two fulcrums F1 and F2 which are spaced apart from each other by a distance L. The specimen 1 in the form of a strip is laid on the fulcrums F1 and F2. The width b (direction perpendicular to the sheet surface of FIG. 3) and thickness t of the substrate 1b are measured beforehand. The indenter 4 is implemented by a PZT AE transducer which is formed into a spherical tip with a tip radius of 5 to 10 millimeters. The adhesion force can be obtained by the formula (2).

Figure 4:
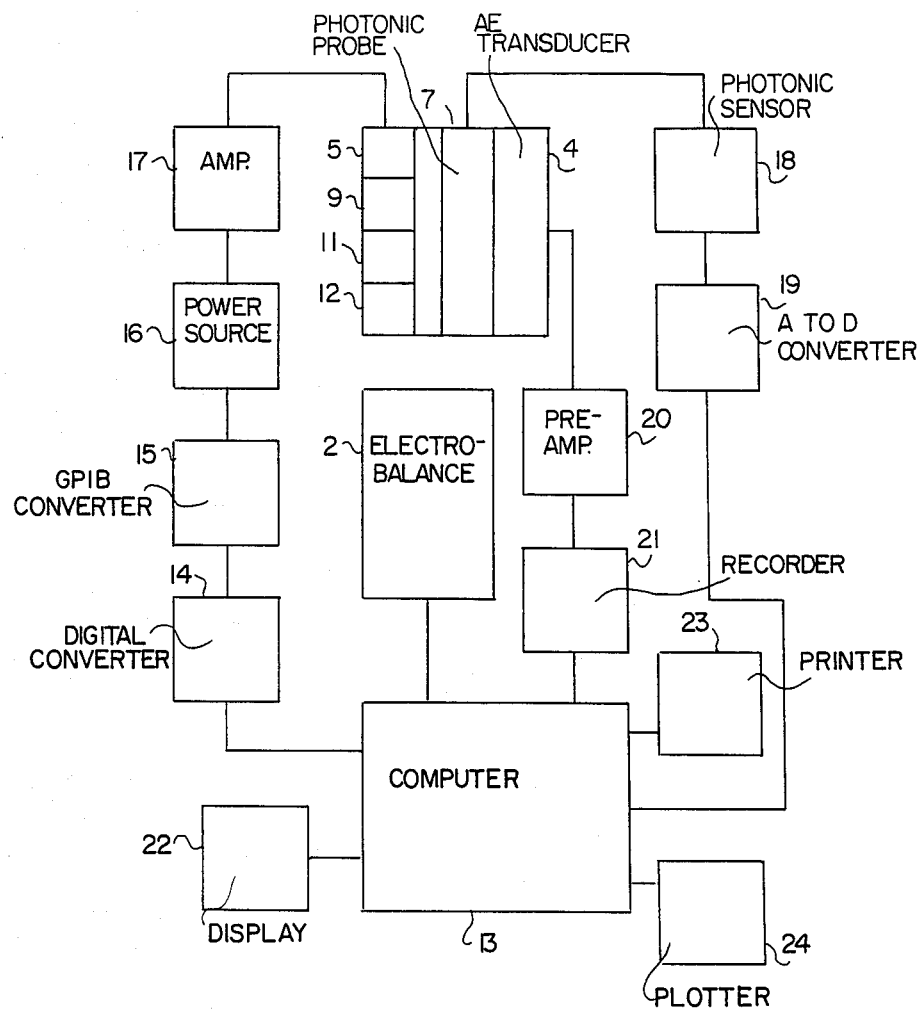
FIG. 4 is a block diagram showing an embodiment of the present invention.

FIG. 4 is a schematic block diagram representative of a control and data processing system which is applicable to any of the embodiments shown and described. As shown, the measuring apparatus is controlled by a personal computer 13. Specifically, control signals from the computer 13 are applied to the piezoelectric actuators 5, 9, 11 and 12 via a digital converter 14, a general purpose interface bus (GPIB) converter 15, a constant voltage power source 16, and a voltage amplifier 17, whereby those actuators 5, 9, 11 and 12 are controllably driven. The drive speed of the piezoelectric actuators 5, 9, 11 and 12 are each variable over a wide range between 10 angstroms per second and 20 microns per second. The load applied to the specimen 1 is directly fed from the electrobalance 2 to the personal computer 13 as a digital signal. The penetration depth $\delta$ of the indenter 4 is measured by converting light from the Photonic Probe 7 into voltage by use of a Photonic Sensor (tradename and also available from Photonics, U.S.A.) 18.

The voltage signal from the Photonic Sensor 18 is routed through an analog-to-digital converter 19 to the personal computer 13. The AE signal from the AE transducer of the indenter 4 is fed via a preamplifier 20 to a highspeed data recorder 21 to be processed by the personal computer 13. Processing the incoming data, the personal computer 13 analyzes the frequency distribution, amplitude distribution and count (number of acoustic emissions occurred) to detect an AE signal which is derived from the separation of the thin film 1a from the substrate 1b. The load, the displacement and the AE signals may be fed to a display 22, a printer 23 and/or an X-Y plotter 24 after being processed by the personal computer 13.

The electrobalance 2 which serves as a load transducer has a resolution of 0.1 microgram. While the load transducer may be implemented by a differential transformer type transducer, an electrobalance 2 is most desirable because it is little susceptible to mechanical vibrations and has no effect on the measurement of displacement.

For the Photonic Probe 7 and Photonic Sensor 18 which cooperate as a displacement gauge, use may be made of a sheet of glass coated with gold, platinum or palladium which undergoes a minimum of aging. Such a sheet allows the displacement to be measured at the sensitivity of 10 angstroms. Alternatively, use may be made of an induction type non-contact displacement gauge.

The indenter 4 implemented by a piezoelectric AE transducer remarkably enhanced the sensitivity in the measurement of the acoustic emissions. Experimental results showed that such a piezoelectric AE transducer is more than 100 times higher in sensitivity than a different type of AE transducer. While the AE transducer may be formed from a piezoelectric material other than the PZT which has been described, e.g., quartz, the PZT is more preferable than the others with respect to the ease of machining and the stability of AE characteristics.

The effectiveness of the apparatus in accordance with the present invention will be discussed in relation to adhesion forces of sputtered carbon films which were actually measured.

Various kinds of specimens were used as listed in Table 1 below. Specifically, Si was deposited on simple rinsed glass substrates and glass substrates with Si (silicon) coatings by RF magnetron sputtering so as to provide carbon films on those substrates. To examine the effect of reverse sputtering on the adhesion force of a carbon film, some specimens were subjected to reverse sputtering for 5 minutes prior to the deposition of carbon films in order to clean the glass substrates or the Si surfaces. Both the Si films and the carbon films were deposited under argon pressure of $40 \times 10^{-3}$ Torr and sputter power of 300 watts.

TABLE 1

| SAMPLE NO. | Si UNDERLAYER | REVERSE SPUTTER | FILM THICKNESS ($\mu$m) |
|---|---|---|---|
| 1 | absent | absent | 0.1 |
| 2 | absent | 50 W | 0.1 |
| 3 | absent | 150 W | 0.1 |
| 4 | absent | 300 W | 0.1 |
| 5 | present | absent | 0.1 |
| 6 | present | 50 W | 0.1 |
| 7 | present | 150 W | 0.1 |
| 8 | present | 300 W | 0.1 |
| 9 | present | 300 W | 0.5 |
| 10 | present | 300 W | 1.5 |
| 11 | present | 300 W | 3.8 |
| 12 | present | 300 W | 6.2 |

The adhesion forces of carbon films on the twelve different specimens shown in Table 1 were measured by the indentation and bending tests of the present invention and the conventional scratching type using the AE sensor. Results of such tests are shown in Table 2 below.

TABLE 2

| SAMPLE NO. | INDENT TYPE (GPa) | BEND TEST TYPE (GPa) | SCRATCH TYPE (PRIOR ART) (N) |
|---|---|---|---|
| 1 | unmeasurable | 0.6 | unmeasurable |
| 2 | 2.0 | 1.0 | unmeasurable |
| 3 | 3.7 | 2.5 | unmeasurable |
| 4 | 4.6 | 3.8 | unmeasurable |
| 5 | unmeasurable | 0.8 | unmeasurable |
| 7 | 5.9 | 5.4 | unmeasurable |
| 8 | 12.6 | unmeasurable | unmeasurable |
| 9 | 10.2 | unmeasurable | unmeasurable |
| 10 | 7.4 | 6.8 | unmeasurable |
| 11 | 3.2 | 2.9 | 2.5 |
| 12 | unmeasurable | 1.3 | 1.6 |

It will be understood that the apparatus of the prevent invention is capable of measuring the adhesion forces of thin films on submicron order.

In Table 2, the word "unmeasurable" implies a condition wherein a signal representative of separation of a substrate and a thin film could not be extracted from the AE signal.

In summary, it will be seen that the present invention provides an apparatus capable of quantitatively evaluating an adhesion force of a thin film whose thickness lies in a submicron range, such evaluation being unattainable with the conventional scratching type apparatus. Basically, the difference between the first and second embodiments of the present invention, i.e., the indentation type apparatus and the bending test type apparatus is that the former is applicable to a range of relatively strong adhesion forces and the latter to a range of relatively weak adhesion forces.

What is claimed is:

1. An apparatus for measuring an adhesion force of a thin film, comprising:
    an inclining mechanism for mounting a sample dish with a specimen including a substrate and a thin film deposited on said substrate, said specimen being inclined by a predetermined angle with respect to said sample dish;
    an indenter disposed above said specimen for deforming said specimen by indentation;
    a driver for driving said indenter perpendicularly to said sample dish;
    a load transducer for measuring a load applied to said specimen by said indenter;
    a sensor for sensing propagation of a crack produced in said specimen by said load;
    a displacement gauge interlocked with said driver for measuring a penetration depth of said indenter; and
    measuring means for measuring said adhesion force of said thin film to said substrate on the basis of said load and said penetration depth at a time when said sensor produces a sense signal and said predetermined angle.

2. An apparatus as claimed in claim 1, wherein said measuring means measures said adhesion force by performing a calculation $(W/\delta^2) \cdot \cos \alpha$ where $\alpha$ denotes said predetermined angle, W denotes said load, and $\delta$ denotes said penetration depth.

3. An apparatus as claimed in claim 1, wherein said sensor includes an acoustic emission sensor.

4. An apparatus as claimed in claim 1, wherein said inclining mechanism is operable to change the angle of inclination.

5. An apparatus as claimed in claim 1, wherein said load transducer includes an electrobalance.

6. An apparatus for determining an adhesion force of a thin film of a substrate, the apparatus comprising:
    a sample dish;
    an inclining mechanism mounted on said sample dish and inclining the specimen by a predetermined angle with respect to said sample dish;
    an indenter disposed above the specimen for deforming the specimen by indentation;
    a driver connected to the indenter for driving the indenter against the specimen, thereby applying a load to the specimen;
    a load transducer for measuring the load applied to the specimen by said indenter, said sample dish being mounted on said load transducer;
    an acoustic emission transducer for sensing propagation of a crack produced in the specimen by the load;
    a displacement gauge cooperatively arranged with said driver for measuring a penetration depth of said indenter; and
    measuring means coupled to said load transducer and said acoustic emission transducer for measuring the adhesion force of the thin film.

7. An apparatus as claimed in claim 6 wherein the acoustic emission transducer includes a plumbum-zironic acid-titanic acid (PZT) piezoelectric ceramic.

8. An apparatus as claimed in claim 6 wherein the indenter has a spherical tip having a radius of approximately 10 microns.

9. An apparatus as claimed in claim 6 wherein said displacement gauge includes:
    a mirror mounted on said sample dish;
    a light-issuing probe mounted on the indenter facing the mirror; and
    a sensor for generating an electronic signal in response to light reflected from the mirror.

10. An apparatus as claimed in claim 9 wherein the mirror includes a sheet of glass coated with one of the group consisting of gold, platinum, and palladium.

11. An apparatus as claimed in claim 6 wherein said driver includes a piezoelectric actuator.

12. An apparatus as claimed in claim 6 wherein said measuring means includes a computer coupled to said inclining mechanism, said load transducer, and said displacement gauge for calculating a value indicative of shearing stress based on a load applied to the specimen, the penetration depth of the indenter, and an angle of the specimen with respect to the horizontal.

* * * * *